(12) United States Patent
Laufer et al.

(10) Patent No.: US 6,494,888 B1
(45) Date of Patent: Dec. 17, 2002

(54) TISSUE RECONFIGURATION

(75) Inventors: Michael D. Laufer, Menlo Park, CA (US); Jeffrey C. Cerier, Franklin, MA (US); Amos G. Cruz, Franklin, MA (US)

(73) Assignee: ndo surgical, Inc., Mansfield, MA (US)

( * ) Notice: Subject to any disclaimer, the term of this patent is extended or adjusted under 35 U.S.C. 154(b) by 0 days.

(21) Appl. No.: 09/574,424

(22) Filed: May 19, 2000

Related U.S. Application Data

(63) Continuation-in-part of application No. 09/520,273, filed on Mar. 7, 2000, and a continuation-in-part of application No. 09/519,945, filed on Mar. 7, 2000.
(60) Provisional application No. 60/140,492, filed on Jun. 22, 1999.

(51) Int. Cl.[7] .............................................. A61B 17/08
(52) U.S. Cl. ........................ 606/153; 606/139; 600/104
(58) Field of Search ................................ 606/219–221, 606/232, 144, 148, 150, 153; 600/104

(56) References Cited

U.S. PATENT DOCUMENTS

| | | |
|---|---|---|
| 3,551,987 A | 1/1971 | Wilinson |
| 5,037,433 A | 8/1991 | Wilk et al. |
| 5,088,979 A | 2/1992 | Filipi et al. ................... 604/26 |
| 5,222,963 A | 6/1993 | Brinkerhoff et al. |
| 5,254,126 A | 10/1993 | Filipi et al. ................. 606/146 |
| 5,346,504 A | 9/1994 | Ortiz et al. ................. 606/192 |
| 5,395,030 A | 3/1995 | Kuramoto et al. |
| 5,403,326 A | 4/1995 | Harrison et al. ............ 606/139 |

(List continued on next page.)

FOREIGN PATENT DOCUMENTS

| | | | |
|---|---|---|---|
| EP | 0 480 428 A2 | 4/1992 | |
| EP | 0 576 265 A2 | 12/1993 | |
| EP | 0 646 356 A2 | 4/1995 | |
| FR | 2 768 324 | 3/1999 | |
| WO | WO 99/22649 | 5/1999 | .......... A61B/17/04 |
| WO | WO 02/24080 | 3/2002 | |

OTHER PUBLICATIONS

International Search Report dated Oct. 16, 2000.
Contractor QQ et al., Endoscopic esophagitis and gastroesophageal flap valve. *J Clin Gastroenterol* 1999 Apr.;28(3):233–7.

(List continued on next page.)

Primary Examiner—David O. Reip
Assistant Examiner—Julian W. Woo
(74) Attorney, Agent, or Firm—Fish & Richardson, P.C.

(57) ABSTRACT

An apparatus includes an elongated member configured for transoral placement into a stomach, and a distal end effector including first and second members configured to engage stomach tissue, e.g., tissue beyond the: esophageal junction. The first and second members are movable relatively toward one another generally in a first plane, and the distal end effector is movable relative to the elongated member in a second plane generally transverse to the first plane. A third member of the distal end effector is configured to engage stomach tissue. The third member is movable in a distal direction relative to the first and second members. A tissue securement member of the apparatus is coupled to at least one of the first and second members for securing together tissue engaged thereby. The tissue securement member includes first and second parts, a suture attached to the first part, and a securing element attached to the suture and configured for engagement with the second part when the first and second members move relatively toward one another to engage tissue, to thereby secure the second part to the first part.

41 Claims, 10 Drawing Sheets

U.S. PATENT DOCUMENTS

| | | | |
|---|---|---|---|
| 5,433,721 A | 7/1995 | Hooven et al. | |
| 5,465,894 A | 11/1995 | Clark et al. | |
| 5,558,665 A | 9/1996 | Kieturakis | 606/1 |
| 5,571,116 A | 11/1996 | Bolanos et al. | 606/143 |
| 5,573,496 A | 11/1996 | McPherson et al. | 600/217 |
| 5,676,674 A | 10/1997 | Bolanos et al. | 606/139 |
| 5,787,897 A | 8/1998 | Kieturakis | 128/898 |
| 5,792,153 A | 8/1998 | Swain et al. | |
| 5,810,882 A | 9/1998 | Bolduc et al. | 606/213 |
| 5,887,594 A | 3/1999 | LoCicero, III et al. | 128/898 |
| 5,897,562 A | 4/1999 | Bolanos et al. | 606/139 |
| 5,901,895 A | 5/1999 | Heaton et al. | |
| 5,984,932 A * | 11/1999 | Yoon | 606/147 |
| 6,009,877 A | 1/2000 | Edwards | |
| 6,086,600 A * | 7/2000 | Kortenbach | 606/139 |
| 6,067,990 A | 8/2000 | Kieturakis | 128/898 |
| 6,113,609 A | 9/2000 | Adams | |
| 6,325,503 B1 | 3/2002 | Matsui et al. | |
| 6,387,104 B1 | 5/2002 | Pugsley, Jr. et al. | |

OTHER PUBLICATIONS

Donahue PE et al., Endoscopic control of gastro–esophageal reflux: status report. *World J Surg* 1992 Mar.–Apr.;16(2):343–6.

Donahue PE et al., Endoscopic sclerosis of the gastric cardia for prevention of experimental gastroesophageal reflux. *Gastrointest Endosc* 1990 May–Jun.;36(3):253–6.

Hill LD and Kozarek RA, The gastroesophageal flap valve. *J Clin Gastroenterol* 1999 Apr.;28(3):194–7.

Hill LD et al., Antireflux surgery. A surgeon's look. *Gastroenterol Clin North Am* 1990 Sep.;19(3):745–75.

Hill LD et al., The gastroesophageal flap valve: in vitro and vivo observations. *Gastrointest Endosc* 1996 Nov.;44(5):541–7.

Hill LD, Intraoperative measurement of lower esophageal sphincter pressure. *J Thorac Cardiovasc Surg* 1978 Mar.;75(3):378–82.

Hill LD, Myths of the esophagus. *J Thorac Cardiovasc Surg* 1989 Jul.;98(1):1–10.

Ismail T et al., Yield pressure, anatomy of the cardia and gastro–oesophageal reflux. *Br J Surg* 1995 Jul.;82(7):943–7.

Jennings RW et al., A novel endoscopic transgastric fundoplication procedure for gastroesophageal reflux: an initial animal evaluation. *J Laparoendosc Surg* 1992 Oct.;2(5):207–13.

Kadirkamanathan SS et al., Antireflux operations at flexible endoscopy using endoluminal stitching techniques: an experimental study. *Gastrointest Endosc* 1996 Aug.;44(2):133–43.

Mason RJ et al., A new intraluminal antigastroesophageal reflux procedure in baboons. *Gastrointest Endosc* 1997 Mar.;45(3):283–90.

McGouran RC and Galloway JM, A laser–induced scar at the cardia increases the yield pressure of the lower esophageal sphincter. *Gastrointest Endosc* 1990 Sep.–Oct.;36(5):439–43.

McGouran RC et al., Does measurement of yield pressure at the cardia during endoscopy provide information on the function of the lower oesophageal sphincter mechanism? *Gut* 1988 Mar.;29(3):275–8.

McGouran RC et al., Is yield pressure at the cardia increased by effective fundoplication? *Gut* 1989 Oct.;30(10):1309–12.

O'Connor KW and Lehman GA, Endoscopic placement of collagen at the lower esophageal sphincter to inhibit gastroesophageal reflux: a pilot study of 10 medically intractable patients. *Gastrointest Endosc* 1988 Mar.–Apr.;34(2):106–12.

Slim K et al., Intraoperative esophageal manometry and fundoplications: prospective study. *World J Surg* 1996 Jan.;20(1):55–9.

Carvalho PJPC et al., Fibrosis of gastric cardia after endoscopic sclerosis. Mechanism for control of experimental reflux? *Am Surg* 1990 Mar.;56(3):163–6.

Kadikramanathan SS et al., An ambulant porcine model of acid reflux used to evaluate endoscopic gastroplasty. *Gut* 1999 Jun.;44(6):782–8.

O'Connor KW et al., An experimental endoscopic technique for reversing gastroesophageal reflux in dogs by injecting inert material in the distal esophagus. *Gastrointest Endosc* 1984 Oct.;30(5):275–80.

Rupp TH and Lehman GA, Endoscopic antireflux techniques. Endoluminal and laparoscopic. *Gastrointest Endosc Clin N Am* 1994 Apr.;4(2):353–68.

Shafik A, Intraesophageal Polytef injection for the treatment of reflux esophagitis. *Surg Endosc* 1996 Mar.;10(3):329–31.

Thor KBA et al., Reappraisal of the flap valve mechanism in the gastrophageal junction. A study of a new valvuloplasty procedure in cadavers. *Acta Chir Scand* 1987 Jan.;153(1):25–8.

Boerema, M.D., "Hiatus hernia: Repair by right–sided, subhepatic, anterior gastropexy," *Surgery*, 65:884–893 (1969).

Cecconello, "Esophagogastric Anastomosis with Valvuloplasty: An Experimental Study," *International Surgery*, 67:121–124 (1982).

Collis, M.D., "Surgical Control of Reflux in Hiatus Hernia," *The American Journal of Surgery*, 115:465–471 (1968).

Collis, M.D., "An Operation for Hiatus Hernia with Short Esophagus," *The Journal of Thoracic Surgery*, 34:768–778 (1957).

Cuschieri, et al., "Multicenter prospective evaluation of laparoscopic antireflux surgery," *Surgical Endoscopy*, 7:505–510 (1993).

DeMeester, M.D. et al., "Nissen Fundoplication for Gastroesophageal Reflux Disease," *Annals of Surgery*, 204:9–20 (1986).

Donahue, M.D., et al., "Endoscopic Control of Gastro–Esophageal Reflux: Status Report," *World Journal of Surgery*, 16:343–346 (1992).

Donahue, M.D., et al., "Endoscopic sclerosis of the gastic cardia for prevention of experimental gastroesophageal reflux," *Gastrointestinal Endoscopy*, 36:253–256 (1990).

Falk, et al., "Laparoscopic Fundoplication: A preliminary report of the technique and postoperative care," *Aust. N.Z. J. Surgery*, 62:969–972 (1992).

Hill, et al., "Surgery for Peptic Esophageal Stricture," 139–147.

Hill, M.D., "An Effective Operation for Hiatal Hernia: An Eight Year Appraisal," *Annals of Surgery*, 166:681–692 (1967).

Hill, et al., "The Esophagus, Medical and Surgical Management," *WB Saunders Co.*, 135–8 (1988).

Hinder, et al. "The Surgical Option for Gastroesophageal Reflux Disease," Symposium on Gastroesophageal Reflux Disease, *Am J Med*, 103:144S–148S (1997).

Ismail, et al., "Yield Pressure: A New Concept in the Evaluation of Gerd?," *AJG*, 91:616–617 (1996).

Jamieson, et al., "The development of surgery for gastro-oesophageal reflux disease," *Surgery of the Oesophagus*, 233–245 (1988).

Jamieson, et al., "Laparoscopic Nissen Fundoplication," *Annals of Surgery*, 220:137–145 (1994).

Janssen, et al., "Prospective randomized comparison of teres cardiopexy and Nissen fundoplication in the surgical therapy of gastro–oesophageal reflux disease," *Br. J.Surg.* 80:875–878 (1993).

Jennings, et al., "A Novel Endoscopic Transgastric Fundoplication Procedure for Gastroesophageal Reflux: An Initial Animal Evaluation," *Journal of Laparoendoscopic Surgery*, 2:207–213 (1992).

Kahrilas, "Gastroesophageal Reflux Disease,"*JAMA*, 276:983–988 (1996).

Kraemer, M.D., et al., "Laparoscopic Hill repair," *Gastrointestinal Endoscopy*, 40:155–159 (1994).

Little, M.D., "Mechanisms of Action of Antireflex Surgery: Theory and Fact," *World Journal of Surgery*, 16:320–325 (1992).

Mason, et al., "Nissen Fundoplication Prevents Shortening of the Sphincter During Gastric Distention," *Arch Surg.*, 132:719–726 (1997).

McGouran, M.D., et al., "A laser–induced scar at the cardia increases the yield pressure of the lower esophageal sphincter," *Gastrointestinal Endoscopy*, 36:439–443 (1990).

McKernan, "Laparoscopic repair of gastroesophageal reflux disease," *Surgical Endoscopy*, 8:851–856 (1994).

Nathanson, et al., "Laparoscopic Ligamentum trees (round ligament) cardioplexy," *Br. J. Surg.*, 78:947–951 (1991).

Nissen, "Eine einfache Operation zur Beeinflussung der Refluxoesophagitis," *Journal Suisee De Medecine*, 590–592 (1956).

O'Connor, et al., "Endoscopic placement of collagen at the lower esophageal sphincter to inhibit gastroesophageal reflux: a pilot study of 10 medically intractable patients," *Gastrointestinal Endoscopy*, 34:106–112 (1988).

Pedinielli, "Traitement Chirurgical de la Herinie Hiatale Par La Technique du Collet", *Ann. Chir.*, 18:1461–1474 (1964). (English Abstract).

Polk, et al. "Hiatol Hernia and Esophagitis: A survey of indications for operation and technic and results of fundoplication," *Ann. Surg.*, 173:775–781 (1971).

Rampal, et al., "Technique Chirurgicale, Traitement des hernies hiatales et du reflux aesophagien par la cardio–pexie avec le ligament round de foie," *La Presse Medicale*, 75:617–619 (1967).

Rich, "Simple GERD Treatment Offers New Alternative, "(www.medicalpost.com website), Mar. 1999.

Singh, et al., "Evaluation of the Endoscopic Suturing System in the Treatment of GERD," *DDW*, May 16–19, 1999.

Skinner, et al., "Surgical management of esophageal reflux and hiatus hernia," *Journal of Thoracic and Cardiovascular Surgery*, 53:33–54 (1967).

Starling, et al. Assessment of the Anglechik Prosthesis for Treatment of Symptomatic Esophageal Reflux, *World J. Surg.* 11, 350–355 (1987).

Tocornal, M.D., et al., "A mucosol flap valve mechanism to prevent gastroesophageal reflux and esophagitis," *Surgery*, 64:519–523 (1968).

Wang, et al., "A new anti–flux procedure: cardiac oblique invagination," *Chung Hua Wai Ko Tsa Chih*, Feb.; 33 (2) 73–5 (1995). (English Abstract).

Watson, et al., "Comparison of anterior, posterior and total fundoplication using a viscera model," *Diseases of the Esophagus*, 10: 110–114 (1997).

Westbrook, et al., "Posterior Surgical Approaches to the Rectum," *Annals of Surgery*, 195:677–691 (1982).

* cited by examiner

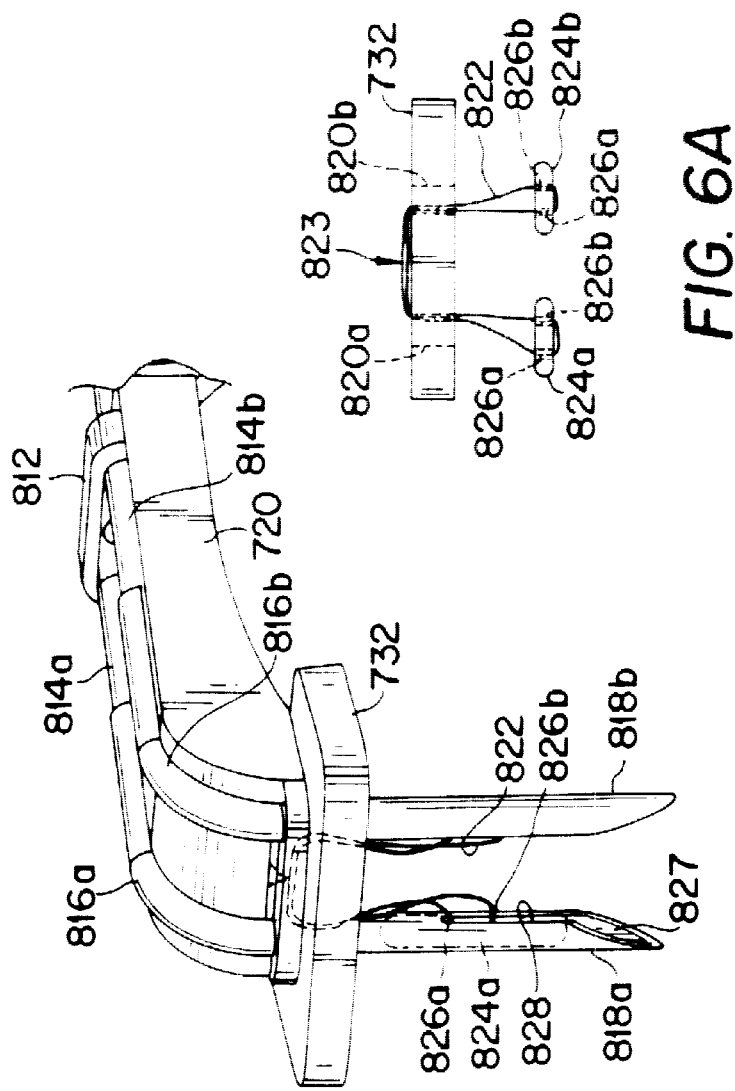
FIG. 6A
FIG. 6B
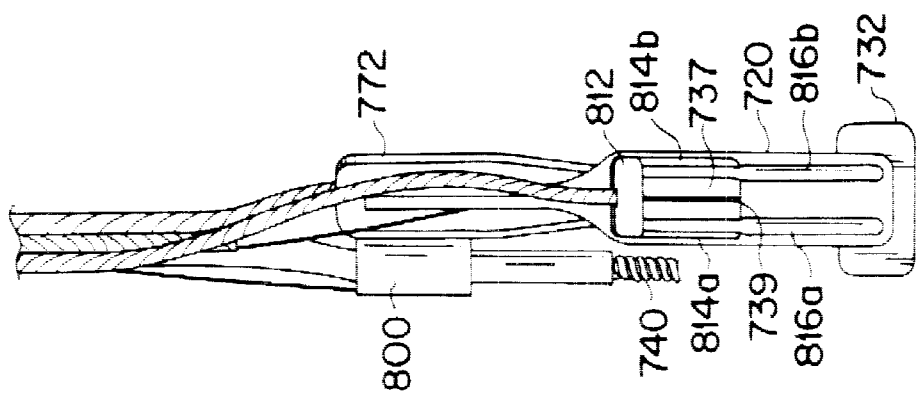
FIG. 5

TISSUE RECONFIGURATION

This application is a continuation-in-part of copending application U.S. Ser. No. 09/520,273, filed Mar. 7, 2000, entitled METHODS AND DEVICES FOR TISSUE RECONFIGURATION, hereby incorporated by reference, and copending application U.S. Ser. No. 09/519, 945, filed Mar. 7, 2000, entitled DEVICE AND METHOD FOR CORRECTION OF A PAINFUL BODY DEFECT, hereby incorporated by reference, both of which claim priority from provisional application U.S. Serial No. 60/140,492, filed Jun. 22, 1999, entitled STOMACH ELEVATOR METHOD AND DEVICE, hereby incorporated by reference.

BACKGROUND

This invention relates to methods and apparatus for reconfiguring tissue, and more particularly to reconfiguring tissue in the vicinity of the gastroesophageal junction.

Gastroesophageal reflux disease (GERD) is a common upper-gastrointestinal disorder in which acidic contents of the stomach flow inappropriately from the stomach into the esophagus. Backflow of gastric contents into the esophagus results when gastric pressure is sufficient to overcome the resistance to flow that normally exists at the gastroesophageal junction (GEJ) or when gravity acting on the contents is sufficient to cause flow through the GEJ. Medication, open surgical procedures, minimally invasive surgical techniques, and endoscopic techniques are known for treating GERD.

SUMMARY

According to one aspect of the invention, an apparatus includes an elongated member configured for transoral placement into the stomach, and a distal end effector including first and second members configured to engage stomach tissue, e.g., stomach tissue beyond the esophageal junction. The first and second members are movable relatively toward one another generally in a first plane, and the distal end effector is movable relative to the elongated member in a second plane generally transverse to the first plane.

Embodiments of this aspect of the invention may include one or more of the following features.

The distal end effector includes a third member configured to engage stomach tissue. The third member is movable in a distal direction relative to the first and second members. The third member includes a tissue engaging portion, e.g., a coil having a tissue penetrating tip.

The apparatus includes a tissue securement member for coupling to at least one of the first and second members for securing together tissue engaged thereby. The tissue securement member includes a first part for coupling to the first member for engagement with a first tissue section, a second part for coupling to the second member for engagement with a second tissue section to be secured to the first tissue section, a suture attached to the first part, and a securing element attached to the suture and configured for engagement with the second part when the first and second members are moved relatively toward one another to engage the first and second tissue sections, thereby to secure the second part to the first part. The securing element is configured for deployment from the first member, and the first member includes a deploying element for deploying the securing element from the first member. The first member includes tissue piercing elements defining a channel for receiving securing elements.

The second plane is generally perpendicular to the first plane. The distal end effector is configured for movement between a first position generally aligned with the elongated member and a second position in which the distal end effector has moved in the second plane out of alignment with the elongated member. A cable actuatable from a proximal end of the apparatus and coupled to the distal end effector moves the distal end effector in the second plane. A cable actuatable from the proximal end of the apparatus and coupled to the distal end effector moves the first and second members generally in the first plane.

The elongated member defines a channel for receiving an endoscope.

According to another aspect of the invention, a method includes advancing an apparatus including an elongated member transorally into the stomach. The apparatus includes a distal end effector having first and second members configured to engage stomach tissue. The first and second members are movable relatively toward one another generally in a first plane. The method includes then moving the distal end effector relative to the elongated member in a second plane generally perpendicular to the first plane to position the first and second members for engagement with the tissue.

Embodiments of this aspect of the invention may include one or more of the following features.

The first and second members are moved relatively toward one another in the first plane to engage tissue, e.g., stomach tissue beyond the esophageal junction. Moving the first and second members engages a first tissue section with a first securing part and a second tissue section with a second securing part. The first securing part includes a suture attached thereto and a securing element attached to the suture. The method includes moving the securing element into engagement with the second securing part to secure the second securing part to the first securing part. Moving the first and second members causes tissue piercing elements of the first member to pierce tissue. Securing elements are deployed through the tissue piercing elements.

The method further includes piercing the tissue with a third member of the distal end effector prior to engaging the tissue with the first and second members.

The instrument and method of the invention advantageously provide an endoscopic approach to treating GERD that does not require the surgical formation of portals to access the GEJ. The procedure can be performed as an outpatient procedure done under sedation, without general anesthesia being required. The procedure can be performed by gastroenterologists rather than a surgeon, and takes less time, has fewer complications and side-effects and has lower overall procedure costs than surgical methods. The procedure recreates or augments the natural anatomy, and is easily reversible.

Other features, objects, and advantages of the invention will be apparent from the following detailed description, and from the claims.

DESCRIPTION OF DRAWINGS

FIG. 5 is a side view of the distal end of the instrument, turned 90 degrees relative to FIG. 4A;

FIG. 6A is an illustration of a first part of the tissue fixation device of FIG. 2;

FIG. 6B is an illustration of the first jaw member with the first part of the tissue fixation device mounted to the jaw member;

DETAILED DESCRIPTION

Figure 1:
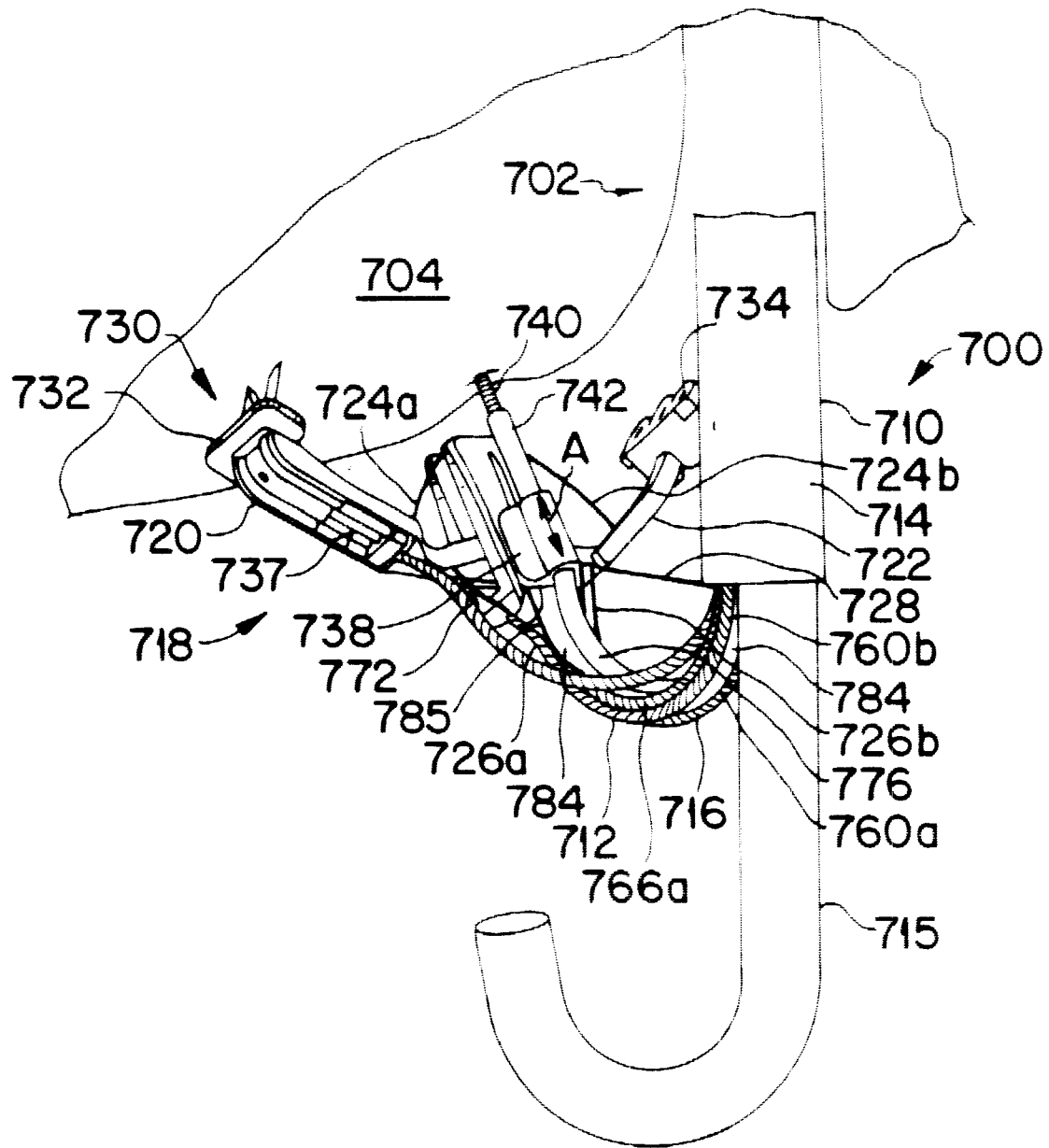
FIG. 1 is a diagrammatic representation of an instrument in use to reconfigure tissue in the vicinity of the gastroesoplageal junction of the stomach.

Referring to FIG. 1, an instrument 700 for reconfiguring stomach tissue, e.g., stomach tissue in the vicinity of the gastroesophageal junction (GEJ) 702, such as tissue 704 of the lesser curvature of the stomach, is shown. The GEJ is the region of transition from the esophagus to the stomach. The lesser curvature of the stomach is a portion of the stomach located beyond the GEJ. Instrument 700 includes an elongated shaft 710 dimensioned to permit transoral access, to the stomach, and a tissue manipulator 712 for manipulating stomach tissue. Positioned within a lumen 714 defined by shaft 710 is a standard GI endoscope 715 providing visual guidance of the reconfiguring procedure. Instrument 700 is particularly adapted for treating GERD. Using instrument 700, as described below, a bulge, plication or tissue wrap is formed in the vicinity of gastroesophageal junction 702 to reduce reflux of stomach fluids into the esophagus.

Figures 2, 3A:
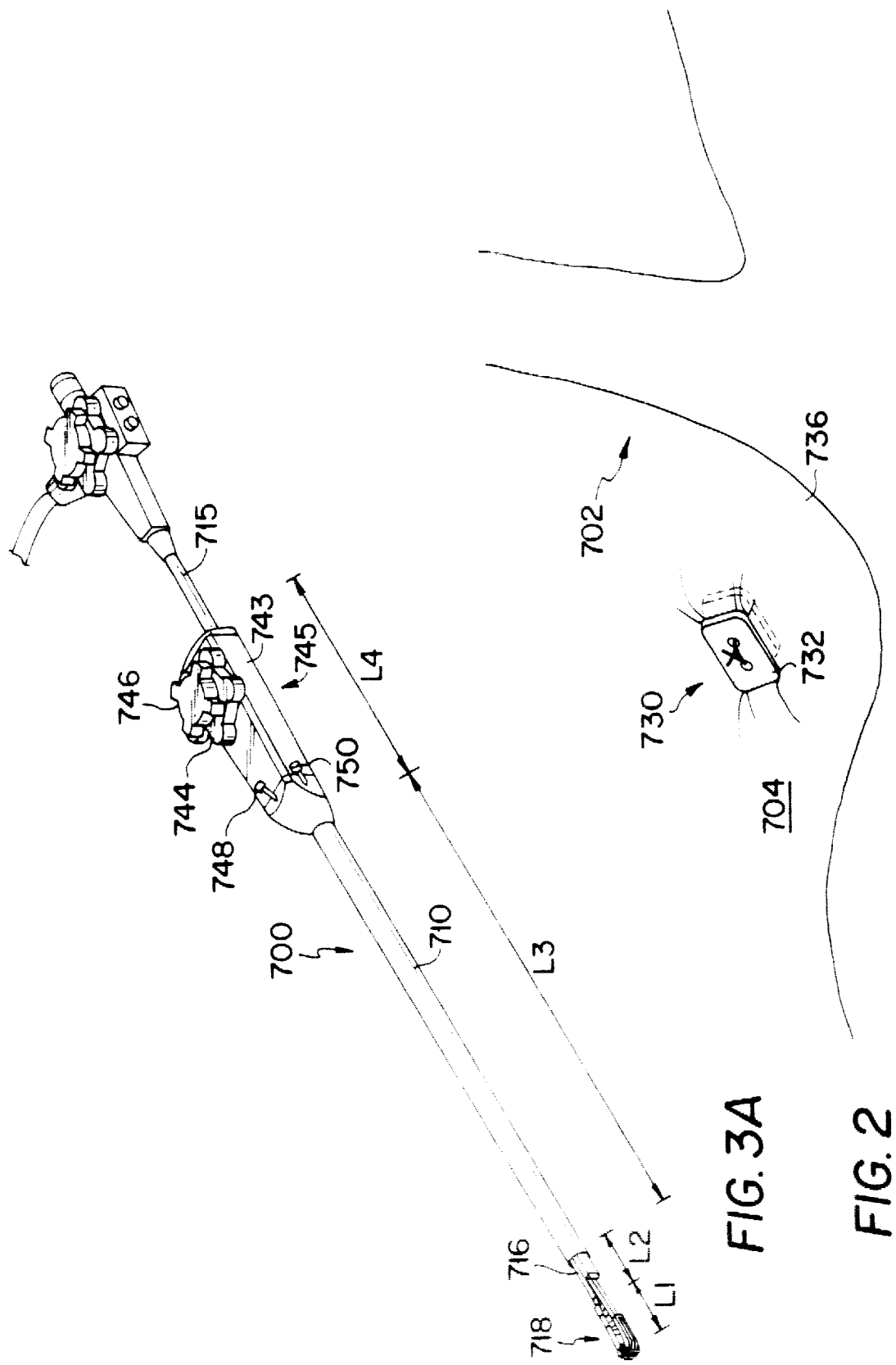
FIG. 2 shows a tissue fixation device deployed by the instrument of FIG. 1 in use to secure a bulge formed in the tissue.
FIG. 3A is an illustration of the instrument of FIG. 1.

Tissue manipulator 712 has an elongated cable assembly 716 housed within lumen 714 of shaft 710, and a distal end effector 718 actuated to perform the various steps in the tissue reconfiguring procedure by cable assembly 716. End effector 718 includes first and second jaw members 720, 722 which engage tissue 704. Cable assembly 716 includes first and second cable pairs 724a, 724b, and 726a, 726b for moving jaws 720, 722 relatively toward and away from one another, respectively, in a first plane, and a third cable 728 for moving end effector 718 relative to shaft 710 in a second plane generally transverse to, and preferably perpendicular to, the first plane, as described further below. During insertion into the stomach, end effector 718 is aligned with shaft 710 (as shown in FIG. 3A). Once positioned in the stomach, cable 728 is actuated to articulate end effector 718 out of alignment with shaft 710 (as shown in FIG. 1).

Cable assembly 716 includes a spring beam 784, formed from, e.g., stainless steel, extending into shaft 710. End effector 718 is attached to beam 784 at a distal end 785 of beam 784. Beam 784, in its rest state, is biased toward a straight alignment. Pulling cable 728 bends beam 784. When cable 728 is released, beam 784 returns toward the straight alignment.

Referring also to FIG. 2, mounted to first jaw 720 is a first part 732 of a tissue securement member, e.g., a fixation device 730, and mounted to second jaw 722 is a second part 734 of tissue fixation device 730. As described further below, after jaws 720, 722 engage tissue 704 and manipulate the tissue in a wrapping action to create a bulge 736 in, e.g., the lesser curvature of the stomach, tissue fixation device 730 is deployed to secure the engaged tissue together. Cable assembly 716 includes a fourth cable 737 for deploying fixation device 730, as described further below.

End effector 718 further includes a tube 738 and a third tissue engaging member, e.g., a coil 740, received within tube 738, for purposes described below. Coil 740 is housed within an overtube 742, and coil 740 and overtube 742 can be moved axially proximally and distally relative to jaws 720, 722, along the axis, A, of cable assembly 716. Coil 740 can be rotatably advanced into tissue.

Figure 3B:
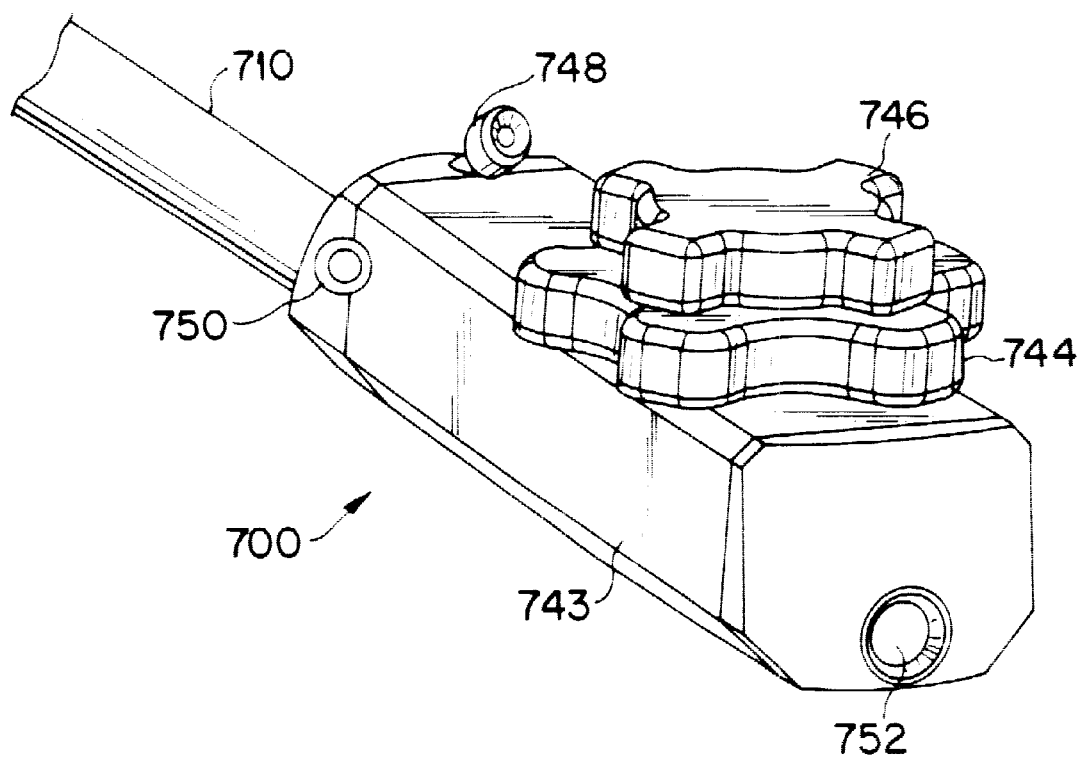
FIG. 3B shows a proximal end of the instrument.

Referring to FIG. 3A, instrument 700 has, at its proximal end 745, a handle 743 with a control knob 744 for controlling cables 724a, 724b, 726a, 726b to close and open jaws 720, 722, and a control knob 746 for controlling cable 728 to move end effector 718. Handle 743 includes a port 748 through which coil 740 and overtube 742 can be introduced into shaft lumen 714, and a pull-knob 750 for deploying tissue fixation device 730, as described below. As shown in FIG. 3B, handle 743 defines a channel 752 through which endoscope 715 is introduced into shaft lumen 714.

Figure 3C:
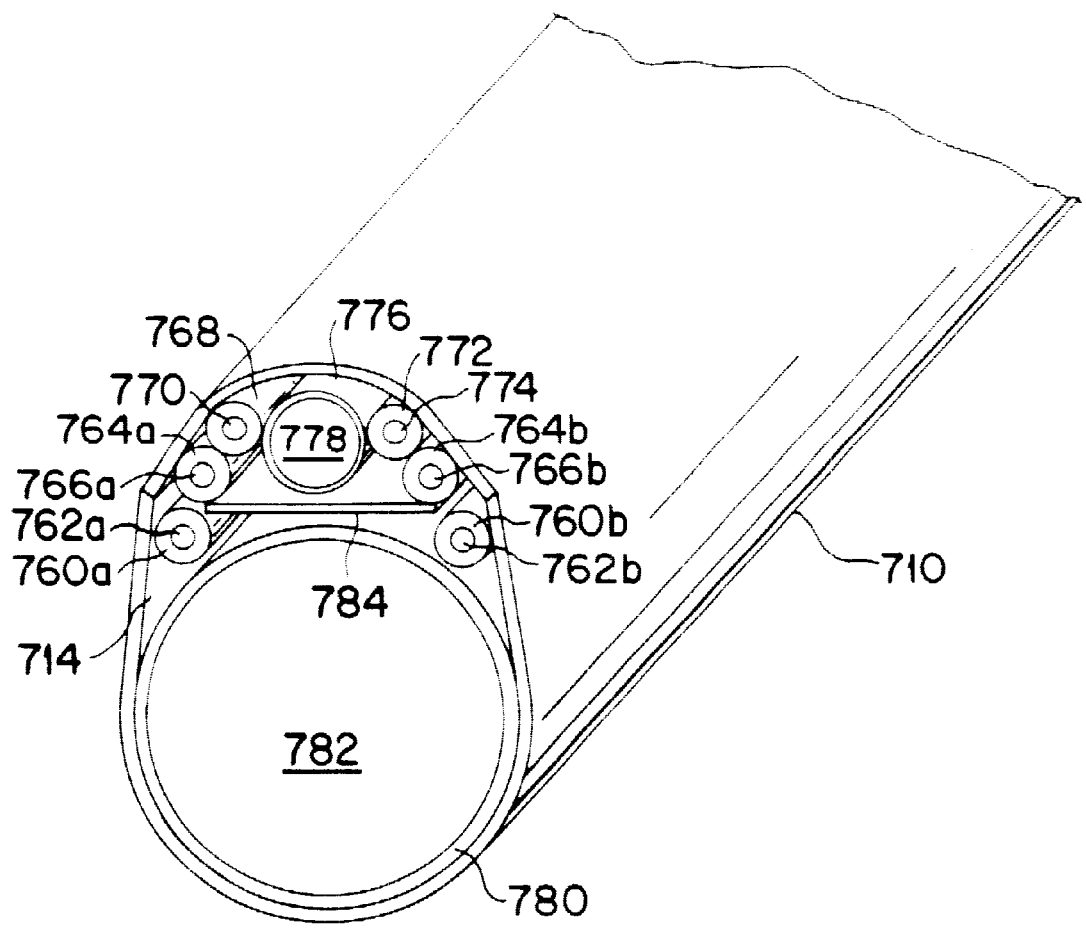
FIG. 3C shows the working channels in a shaft of the instrument.
Figure 3D:
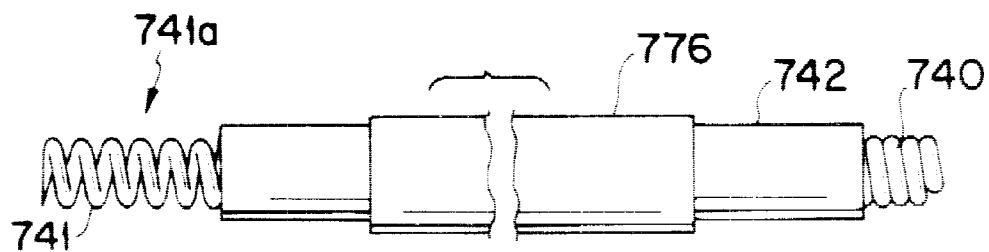
FIG. 3D is an illustration of a coil assembly of the instrument.

Referring to FIGS. 1 and 3C, which shows the working channels in shaft 710 for receiving the various cables, overtube 742 and endoscope 715, within lumen 714 of shaft 710 are cable housings 760a, 760b defining channels 762a, 762b in which cables 724a, 724b for closing jaws 720, 722 are received, and cable housings 764a, 764b defining channels 766a, 766b in which cables 726a, 726b for opening jaws 720, 722 are received. Within lumen 714 are also a cable housing 768 defining a channel 770 in which cable 728 for bending end effector 718 is received, and a cable housing 772 defining a channel 774 in which cable 737 for deploying fixation device 730 is received. Coil 740 and overtube 742 are received in a channel 778 defined in a coil housing 776 in lumen 714. Housing 776 extends from port 748 to tube 738. As shown in FIG. 3D, coil 740 has a tissue penetrating tip 741 and a distal section 740a having a looser wound coil than the remainder of coil 740. Endoscope 715 is received in a channel 782 defined in an endoscope housing 780 in lumen 715.

Spring beam 784 is located generally between cable housing 776 and endoscope housing 780, and extends about 4 inches into shaft 710 from the distal end of the shaft where beam 784 is mounted to shaft 710 by, e.g., silicone adhesive/sealant. The various cable housings and spring beam 784 do not move relative to shaft 710 and handle 743. It is the movement of the cables within the cable housings that actuate end effector 718. Shaft 710 is preferably formed from, e.g., heat-shrink tubing.

Referring again to FIG. 3A, end effector 718 has a length, L1, of about 2 inches, cable assembly 716 extends axially by a length, L2, of about 2.5 inches from shaft 710, shaft 710 has a length, L3, of about 23.5 inches, and handle 743 has a length, L4, of about 5 inches. Cable assembly 716, spring beam 784, and shaft 710 have the necessary flexibility to permit transoral placement of instrument 700 into the stomach. The length, L1, of relatively rigid end effector 718 is minimized to ensure the necessary flexibility of instrument 700 is maintained. The distance that cable assembly 716 extends axially from shaft 710 is selected to cantilever beam 784 permitting the desired bending of end effector 718 relative to shaft 710 to position jaws 720, 722 against the inner surface of the stomach in the vicinity of the GEJ.

Distal end effector 718 is sized to fit through a 12–16 mm diameter channel (corresponding to the diameter of the esophagus) and shaft 710 has an outer diameter of about 12 to 16 mm to enable transoral passage of instrument 700 into the stomach. Scope channel 782 has a diameter of either about 8 mm or 10 mm. An 8 mm diameter scope channel allows passage of 7.9 mm pediatric gastroscope, and a 10 mm diameter scope channel allows passage of a 9.8 mm adult gastroscope. Channel 778 has a diameter of about 2–3 mm for receiving cable 742.

Figure 4A:
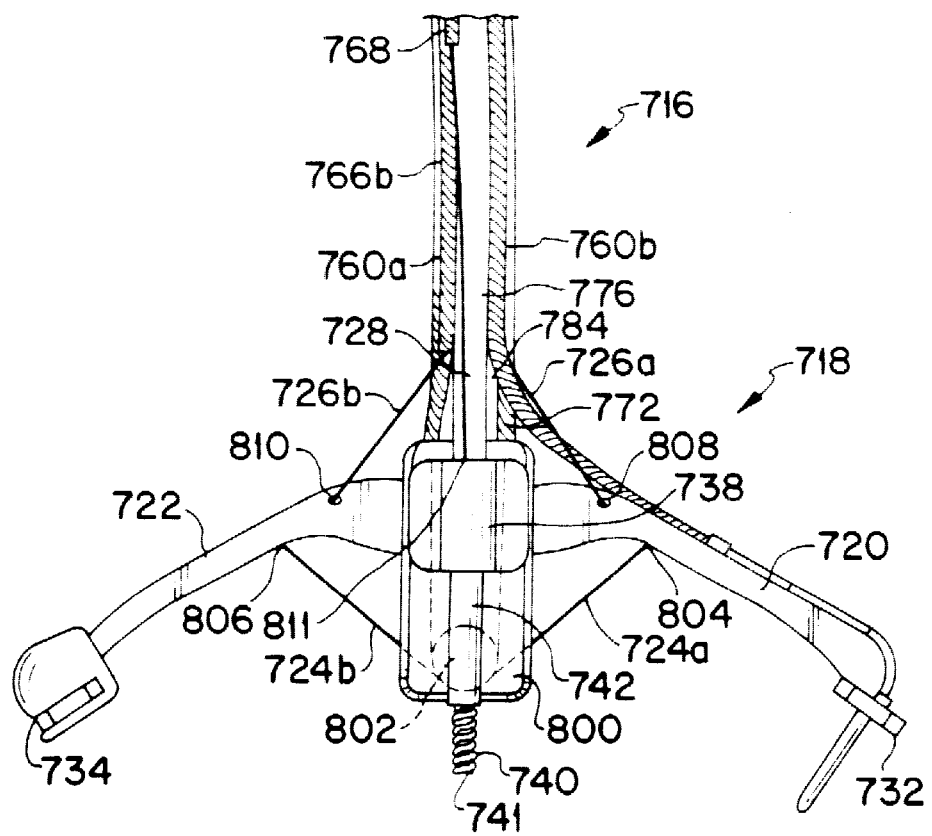
FIG. 4A is a top view of a distal end of the instrument, shown with first and second jaw members in an open position.
Figure 4B:
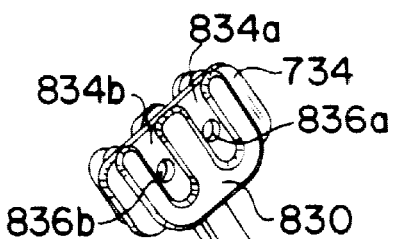
FIG. 4B shows the distal end of the instrument located off-axis relative to a shaft of the instrument.
Figure 4B:
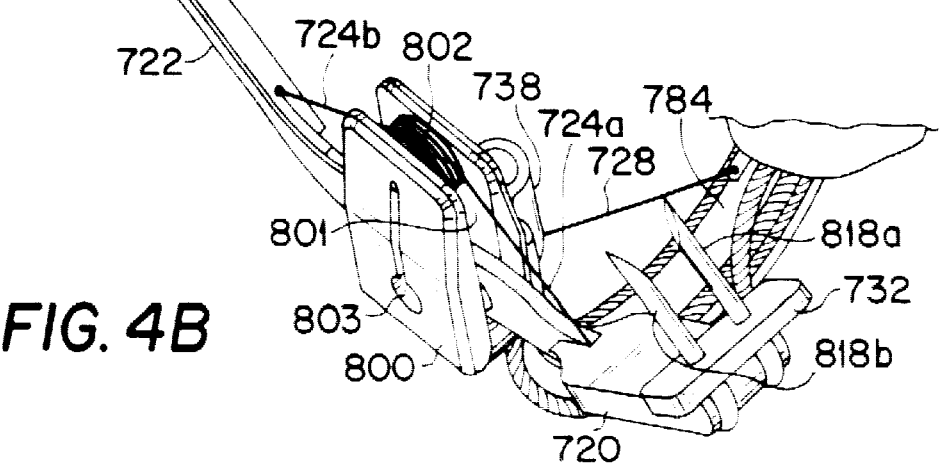

Distal end effector 718 is shown in more detail in FIGS. 4A and 4B. End effector 718 includes a central mount 800 defining a slot 801. Spanning slot 801 and supported by mount 800 is a pin 803 to which 720, 722 are pivotally mounted. Central mount 800 also houses two pulleys 802 over which cables 724a, 724b are respectively passed for closing jaws 720, 722. Cables 724a, 724b terminate at points 804, 806 on jaws 720, 722, respectively. Cables 726a, 726b for opening jaws 720, 722 terminate at points 808, 810 on jaws 720, 722, respectively, proximal of points 804, 806. Tube 738 of end effector 718 for receiving coil 740 and overtube, 742 is attached to mount 800, and cable 728 for bending end effector 718 terminates at point 811 on tube 738.

Pulling cables 724a, 724b proximally moves jaws 720, 722 toward one another generally in a first plane (in the plane of the paper in FIG. 4A). Pulling cables 726a, 726b proximally moves jaws 720, 722 away from one another generally in the first plane. Pulling cable 728 proximally bends beam 784 moving end effector 718 in a second plane (out of the plane of the paper in FIG. 4A) generally perpendicular to the first plane.

Referring also to FIG. 5, jaw 720 includes two guide tubes 816a, 816b and a slider 812 including two push rods 814a, 814b guided within tubes 816a, 816b, respectively. Slider 812 is mounted to jaw 720 to slide relative to jaw 720. Tubes 816a, 816b curve about jaw 720 to terminate in tissue penetrating tips 818a, 818b (FIG. 6B), respectively. Push rods 814a, 814b can be formed from molded plastic such as polyethylene or polypropylene or as a braided stainless steel cable to provide the flexibility to follow the curve of tubes 816a, 816b. Cable housing 772 is attached to slider 812 and cable 737 terminates at a fixed point 739 on jaw 720. Actuation of cable 737 pushes slider 812 distally, as described below.

First part 732 of tissue fixation device 730 is shown in more detail in FIGS. 6A and 6B. First part 732 of tissue fixation device 730 defines through holes 820a, 820b (FIG. 6A), and part 732 is loaded onto jaw 720 with tips 818a, 818b received in through holes 820a, 820b, respectively. Connected to part 732 with a suture 822 are two securing elements, e.g., bars 824a, 824b. Each bar 824a, 824b defines two through holes 826a, 826b. Suture 822 is threaded through holes 826a, 826b of the bars and through holes 820a, 820b of part 732, and is tied together forming a knot 823 to secure bars 824a, 824b to part 732. Tubes 818a, 818b each define a channel 827 for receiving one of bars 824a, 824b, and a slot 828 communicating with channel 827 for receiving suture 822 therethrough.

Figure 7:
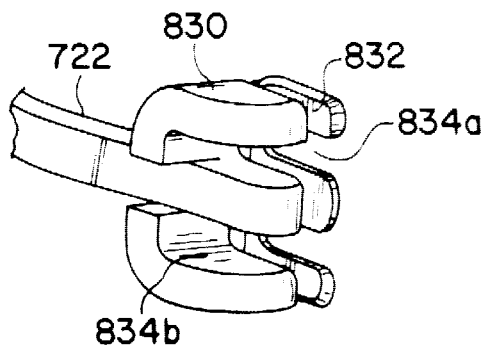
FIG. 7 is an illustration of the second jaw member.
Figure 8:
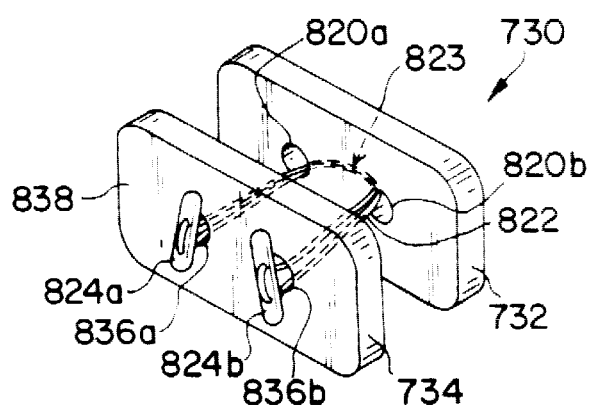
FIG. 8 is an illustration of the tissue fixation device of FIG. 2.

Referring particularly to FIGS. 4B and 7, jaw 722 has a distal member 830 defining a slot 832 for receiving second part 734 of fixation device 730, and slots 834a, 834b for receiving tissue penetrating tips 818a, 818b. Second part 734 of fixation device 730 defines through holes 836a, 836b for receiving tips 818a, 818b. When jaws 720, 722 are closed, tips 818a, 818b pass through slots 834a, 834b and holes 836a, 836b. Actuation of fixation device deployment cable 737 after closing jaws 720, 722 pushes slider 812 and push rods 814a, 814b distally, advancing bars 824a, 824b out of tissue penetrating tips 818a, 818b, and locating bars 824a, 824b on the far side 838 of second part 734 of fixation device 730, as shown in FIG. 8.

Figure 9A:
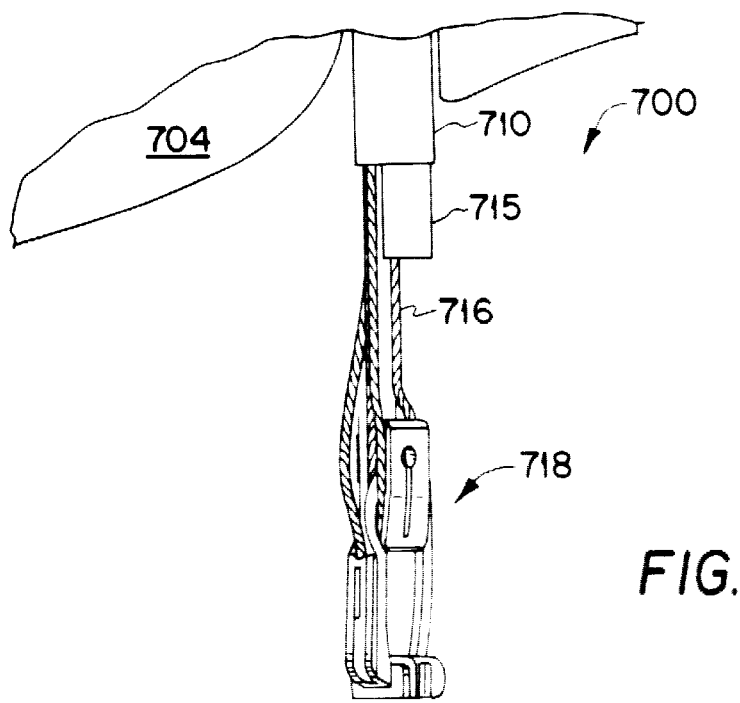
FIGS. 9A–9F show the instrument of FIG. 1 in use.
Figure 9C:
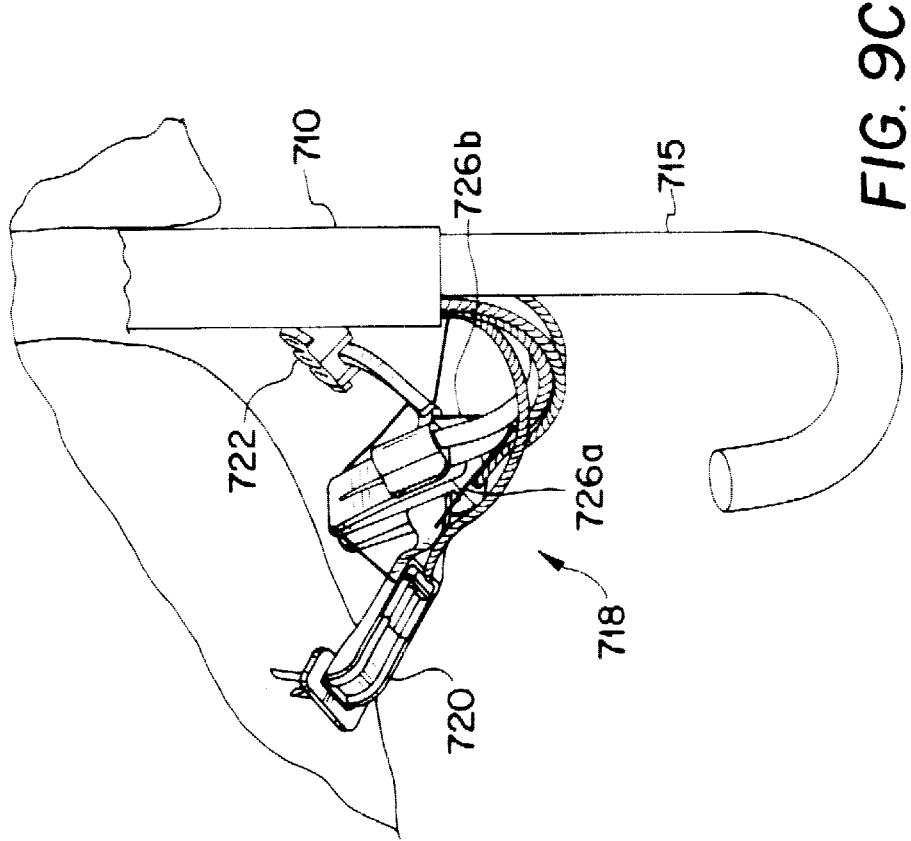
Figure 9B:
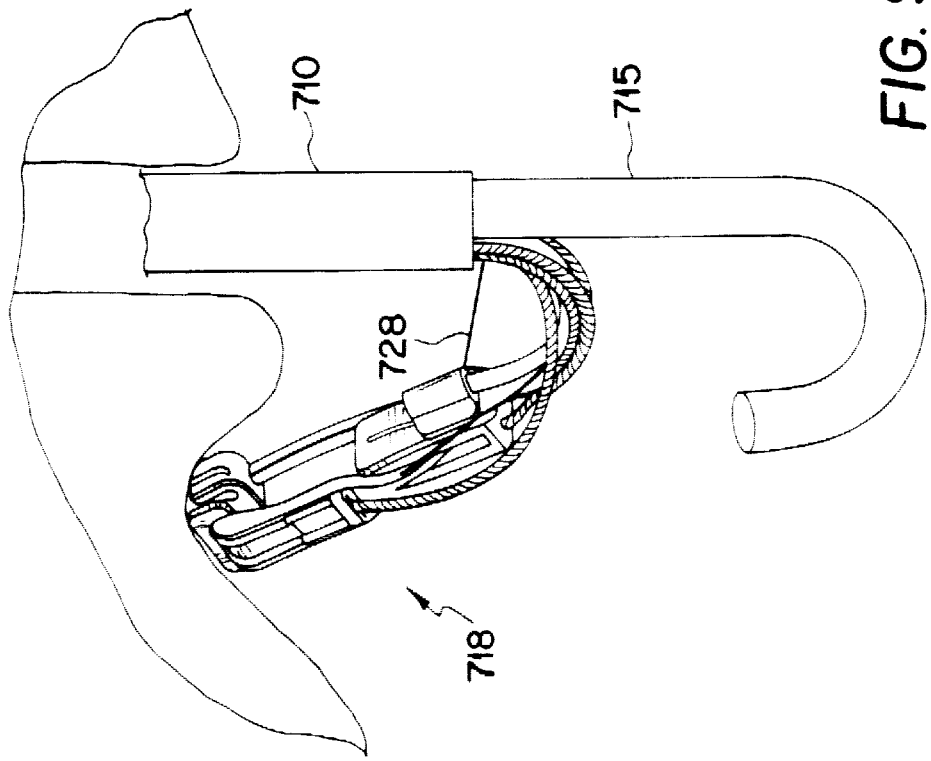

Referring to FIGS. 9A–9F, in use, under endoscopic guidance, the physician advances instrument 700 transorally to position end effector 718 in the stomach. During advancement into the stomach, end effector 718 is generally aligned along the axis of shaft 710, as shown in FIG. 9A. The physician then turns control knob 746 to pull cable 728 proximally, thereby bending beam 784 moving end effector 718 out of alignment with shaft 710 to the position shown in FIG. 9B. By then turning control knob 744 to pull cables 726a, 726b, jaws 720, 722 are pivoted about pins 803 to the open position shown in FIG. 9C.

Figure 9E:
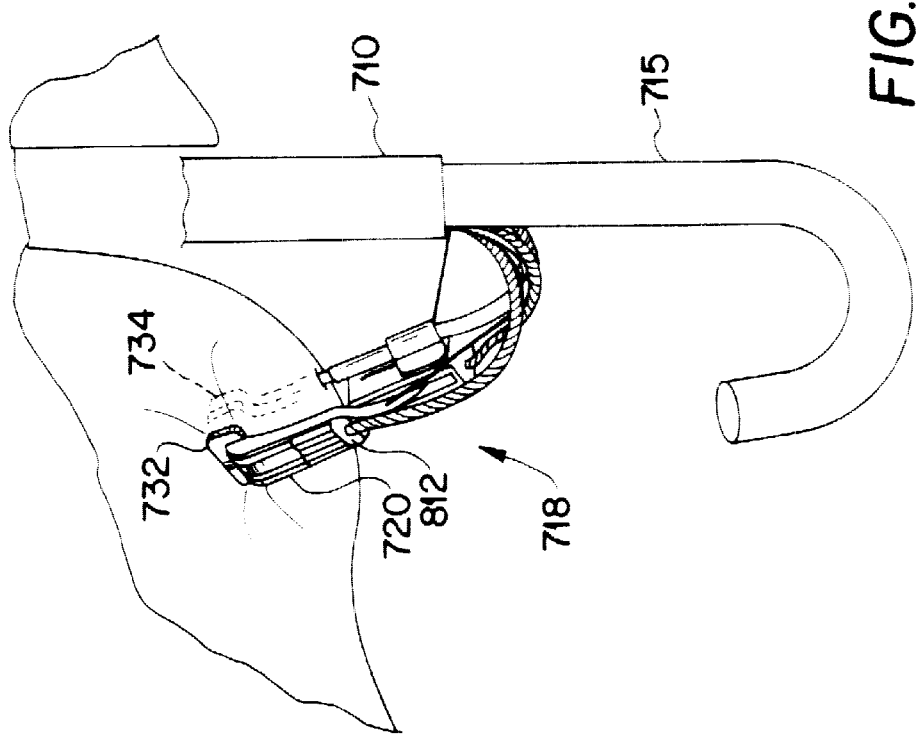
Figure 9D:
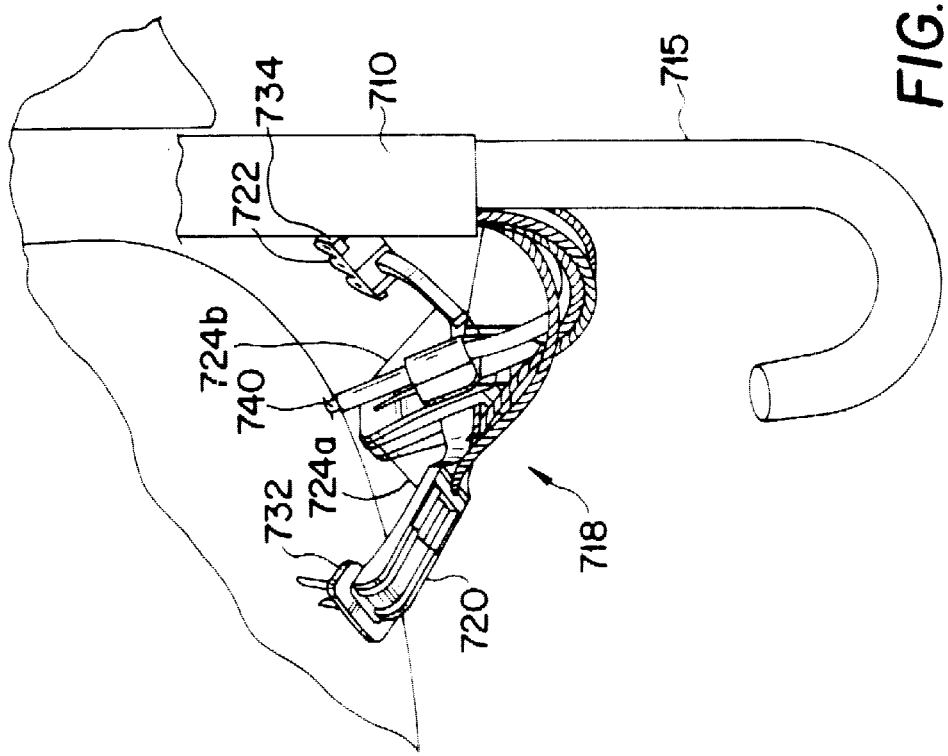

The physician then advances coil 740 and overtube 742 by pushing the coil and overtube distally in channel 778 advancing coil 740 and overtube 742 out of tube 738 and into contact with stomach tissue, preferably stomach tissue beyond the gastroesophageal junction, as shown in FIG. 1. With overtube 742 pressing against the tissue to stabilize the tissue, the physician rotates coil 740 while applying slight distal pressure to advance the coil into the tissue, as shown in FIG. 9D. Coil 740 and overtube 742 are then pulled proximally to pull tissue between jaws 720, 722. Jaws 720, 722 are then closed by turning control knob 744 to pull cables 724a, 724b proximally, as shown in FIG. 9E. The turning of the control knob can also be the action that pulls coil 740 and overtube 742 proximally, ensuring that coil 740 and overtube 742 are positioned out of the way of the closing of the jaws. A lockout can be incorporated to prevent the jaws from closing if coil 740 and overtube 742 are not in their proximal position.

Figure 9F:
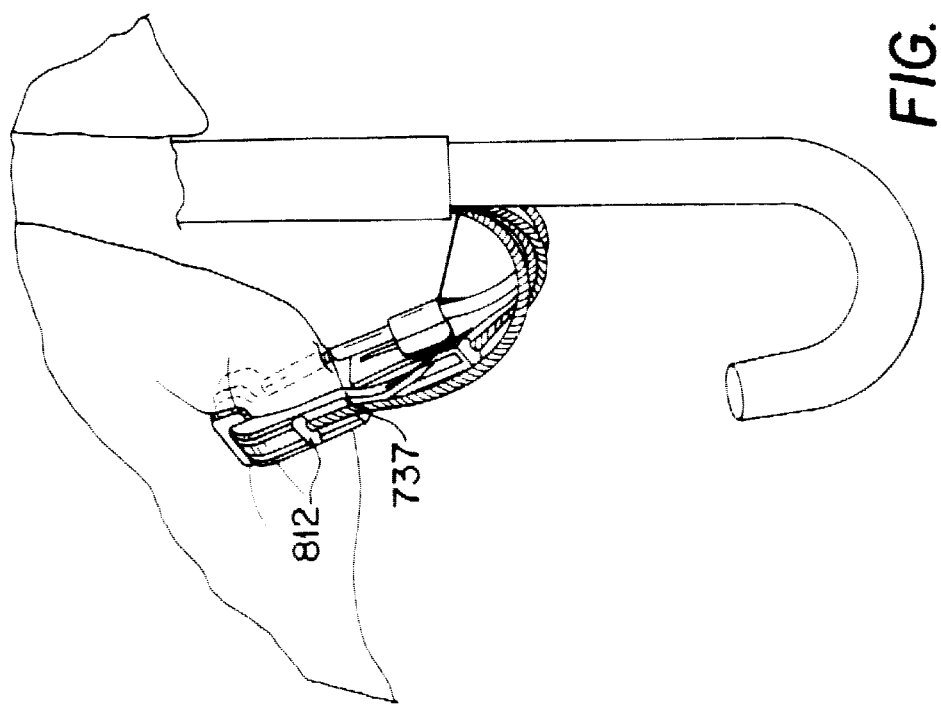

The closing of the jaws places parts 732, 734 of fixation device 730 in contact with two tissue sections, e.g., against two spaced tissue surfaces in the stomach, and causes tissue penetrating tips 818a, 818b to penetrate through the tissue and into holes 836a, 836b in second part 734 of fixation device 730. To deploy fixation device 730, the physician pulls cable 737 proximally removing slack from cable 737. Because cable housing 772 is of fixed length and is non-movably attached to the handle, removing slack from cable 737 causes cable housing 772 to move distally, advancing slider 812 to push t-bars 824a, 824b out of tissue penetrating tips 818a, 818b, as shown in FIG. 9F.

Figure 10:
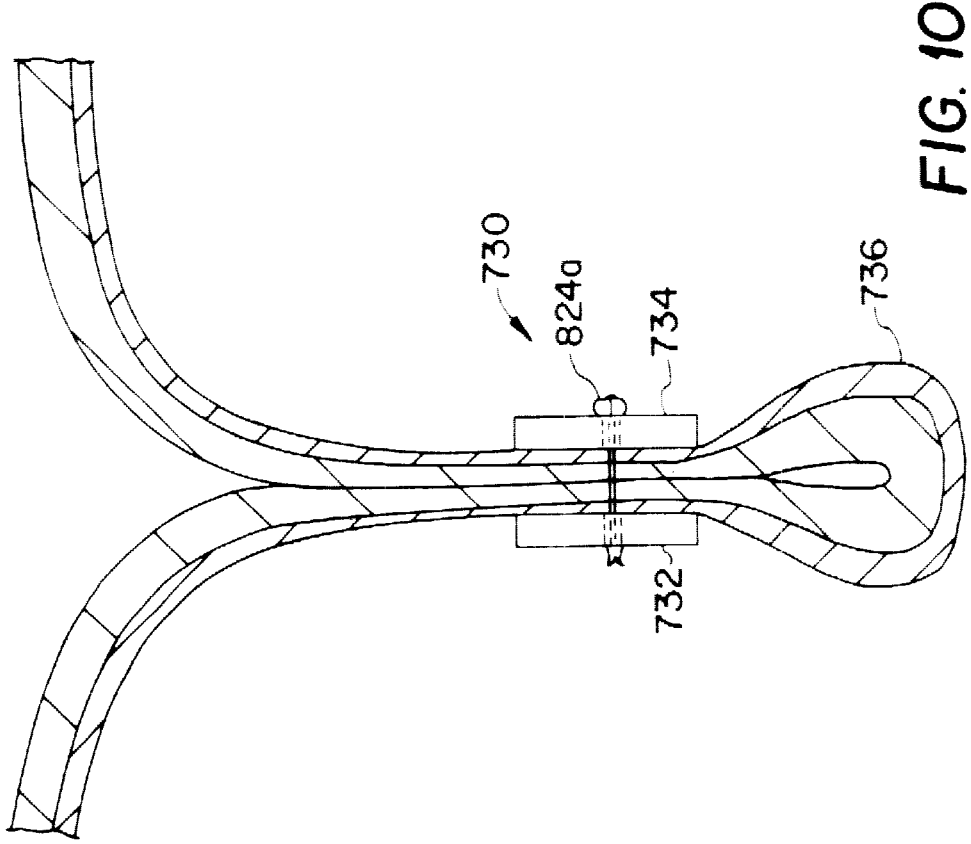
FIG. 10 is an illustration of tissue secured with the tissue fixation device of FIG. 2.

The physician then opens the jaws, disengages jaw 722 from second part 734, returns the distal end effector to its original position generally aligned with shaft 710, closes the jaws and removes instrument 700. FIG. 10 shows a cross-section of the tissue with fixation device 730 in place securing bulge 736.

Other embodiments are within the scope of the following claims.

For example, rather than a coil 740, alternative tissue penetrating or grasping elements such as a T-bar suture or two small grasping jaws can be employed. Instrument 700 can be used without the third tissue, engaging member.

What is claimed is:

1. Apparatus comprising:
    an elongated member configured for transoral placement into a stomach,
    a distal end effector including first and second members configured to engage stomach tissue, the first and second members being movable relatively toward one another generally in a first plane, the distal end effector being movable relative to the elongated member in a second plane generally perpendicular to the first plane, the first member including first and second tissue piercing elements each defining a channel, a third member including a tissue engaging portion for engaging stomach tissue, the third member being movable in a distal direction relative to the first and second members, and a tissue securement member including a first part for coupling to the first member for engagement with a first tissue section, a second part for coupling to the second member for engagement with a second tissue section to be secured to the first tissue section, a suture attached to the first part, and first and second securing elements attached to the suture and deployable through the channels of the first and second tissue piercing elements for engagement with the second part when the first and second members move relatively toward one another to engage the first and second tissue sections, thereby to secure the second part to the first part.

2. A method of treatment, comprising:

engaging first and second regions of stomach tissue with first and second members from within the stomach, and moving the first and second members relatively toward one another to pinch the first and second regions of stomach tissue together thereby reconfiguring tissue in a vicinity of a gastroesophageal junction, the moving of the first and second members engages a first tissue section with a first securing part and a second tissue section with a second securing part and causes a tissue piercing element of the first member to pierce tissue, and moving a securing element of the first securing part into engagement with the second securing part by deploying the securing element through the tissue piercing element to secure the second securing part to the first securing part.

3. The method of claim 2 wherein the moving of the first and second members causes a second tissue piercing element of the first member to pierce tissue, the method further comprising deploying a second element of the securing element through the second tissue piercing element.

4. A method of treatment, comprising:

engaging first and second regions of tissue with first and second members from within the stomach, moving the first and second members relatively toward one another to wrap tissue in a vicinity of a gastroesophageal junction around the gastroesophageal junction, the moving of the first and second members engages a first tissue section with a first securing part and a second tissue section with a second securing part and causes a tissue piercing element of the first member to pierce tissue, and moving a securing element of the first securing part into engagement with the second securing part by deploying the securing element through the tissue piercing element to secure the second securing part to the first securing part.

5. The method of claim 4 wherein the moving of the first and second members causes a second tissue piercing element of the first member to pierce tissue, the method further comprising deploying a second element of the securing element through the second tissue piercing element.

6. A method of treatment, comprising:

engaging first and second regions of tissue with first and second members from within the stomach, and moving the first and second members relatively toward one another to pinch the first and second regions of tissue together in a non-intussuscepting manner thereby reconfiguring tissue in a vicinity of a gastroesophageal junction, the moving of the first and second members engages a first tissue section with a first securing part and a second tissue section with a second securing part and causes a tissue piercing element of the first member to pierce tissue, and moving a securing element of the first securing part into engagement with the second securing part by deploying the securing element through the tissue piercing element to secure the second securing part to the first securing part.

7. The method of claim 6 wherein the moving of the first and second members causes a second tissue piercing element of the first member to pierce tissue, the method further comprising deploying a second element of the securing element through the second tissue piercing element.

8. A method of treatment, comprising:

engaging first and second regions of tissue with first and second members from within the stomach, moving the first and second members relatively toward one another circumferentially relative to a circumference of a gastroesophageal junction to pinch the first and second regions of tissue together thereby reconfiguring tissue in a vicinity of the gastroesophageal junction, the moving of the first and second members engages a first tissue section with a first securing part and a second tissue section with a second securing part and causes a tissue piercing element of the first member to pierce tissue, and moving a securing element of the first securing part into engagement with the second securing part by deploying the securing element through the tissue piercing element to secure the second securing part to the first securing part.

9. The method of claim 8 wherein the moving of the first and second members causes a second tissue piercing element of the first member to pierce tissue, the method further comprising deploying a second element of the securing element through the second tissue piercing element.

10. A method of reconfiguring tissue in the vicinity of a junction between first and second hollow organs, comprising:

engaging first and second regions of tissue of the first organ with first and second members from within the first organ, moving the first and second members relatively toward one another to pinch the first and second regions of tissue of the first organ together thereby reconfiguring tissue in a vicinity of the junction, the moving of the first and second members engages a first tissue section with a first securing part and a second tissue section with a second securing part and causes a tissue piercing element of the first member to pierce tissue, and moving a securing element of the first securing part into engagement with the second securing part by deploying the securing element through the tissue piercing element to secure the second securing part to the first securing part.

11. The method of claim 10 wherein the moving of the first and second members causes a second tissue piercing element of the first member to pierce tissue, the method further comprising deploying a second element of the securing element through the second tissue piercing element.

12. Apparatus comprising:

an elongated member configured for transoral placement into a stomach, a distal end effector including first and second members configured to engage stomach tissue, the first and second members being movable relatively toward one another generally in a first plane, the distal end effector being movable relative to the elongated member in a second plane generally transverse to the first plane, and a third member configured to engage stomach tissue, the third member being movable in a distal direction relative to the first and second members, the third member having a tissue engaging portion including a coil with a tissue penetrating tip.

13. The apparatus of claim 12 wherein the second plane is generally perpendicular to the first plane.

14. The apparatus of claim 12 wherein the distal end effector is configured for movement between a first position generally aligned with the elongated member and a second position in which the distal end effector has moved in the second plane out of alignment with the elongated member.

15. The apparatus of claim 14 further including a cable actuatable from a proximal end of the apparatus and coupled to the distal end effector for moving the distal end effector in the second plane.

16. The apparatus of claim 12 further including a cable actuatable from a proximal end of the apparatus and coupled to the distal end effector for moving the first and second members generally in the first plane.

17. The apparatus of claim 12 wherein the elongated member defines a channel for receiving an endoscope.

18. Apparatus comprising:
an elongated member configured for transoral placement into a stomach,
a distal end effector including first and second members configured to engage stomach tissue, the first and second members being movable relatively toward one another generally in a first plane, the distal end effector being movable relative to the elongated member in a second plane generally transverse to the first plane, and
a tissue securement member for coupling to at least one of the first and second members for securing together tissue engaged thereby.

19. The apparatus of claim 18 wherein the tissue securement member comprises
a first part for coupling to the first member for engagement with a first tissue section,
a second part for coupling to the second member for engagement with a second tissue section to be secured to the first tissue section,
a suture attached to the first part, and
a securing element attached to the suture and configured for engagement with the second part when the first and second members are moved relatively toward one another to engage the first and second tissue sections, thereby to secure the second part to the first part.

20. The apparatus of claim 19 wherein the securing element is configured for deployment from the first member.

21. The apparatus of claim 19 wherein the first member includes a deploying element for deploying the securing element from the first member.

22. The apparatus of claim 18 wherein the second plane is generally perpendicular to the first plane.

23. The apparatus of claim 18 wherein the distal end effector is configured for movement between a first position generally aligned with the elongated member and a second position in which the distal end effector has moved in the second plane out of alignment with the elongated member.

24. The apparatus of claim 23 further including a cable actuatable from a proximal end of the apparatus and coupled to the distal end effector for moving the distal end effector in the second plane.

25. The apparatus of claim 18 further including a cable actuatable from a proximal end of the apparatus and coupled to the distal end effector for moving the first and second members generally in the first plane.

26. The apparatus of claim 18 wherein the elongated member defines a channel for receiving an endoscope.

27. Apparatus comprising:
an elongated member configured for transoral placement into a stomach, and
a distal end effector including first and second members configured to engage stomach tissue, the first and second members being movable relatively toward one another generally in a first plane, the distal end effector being movable relative to the elongated member in a second plane generally transverse to the first plane, the first member including a tissue piercing element.

28. The apparatus of claim 27 wherein the tissue piercing element defines a channel for receiving a securing element.

29. The apparatus of claim 27 wherein the first member includes a second tissue piercing element.

30. The apparatus of claim 29 wherein the second tissue piercing element defines a channel for receiving a securing element.

31. The apparatus of claim 27 wherein the second plane is generally perpendicular to the first plane.

32. The apparatus of claim 27 wherein the distal end effector is configured for movement between a first position generally aligned with the elongated member and a second position in which the distal end effector has moved in the second plane out of alignment with the elongated member.

33. The apparatus of claim 32 further including a cable actuatable from a proximal end of the apparatus and coupled to the distal end effector for moving the distal end effector in the second plane.

34. The apparatus of claim 27 further including a cable actuatable from a proximal end of the apparatus and coupled to the distal end effector for moving the first and second members generally in the first plane.

35. The apparatus of claim 27 wherein the elongated member defines a channel for receiving an endoscope.

36. A method comprising:
advancing an apparatus including an elongated member transorally into the stomach, the apparatus including a distal end effector having first and second members configured to engage stomach tissue, the first and second members being movable relatively toward one another generally in a first plane,
then moving the distal end effector relative to the elongated member in a second plane generally transverse to the first plane to position the first and second members for engagement with the tissue,
engaging tissue by moving the first and second members relatively toward one another generally in the first plane, wherein the moving of the fist and second members engages a first tissue section with a first securing part and a second tissue section with a second securing part, and
moving a securing element of the first securing part into engagement with the second securing part to secure the second securing part to the first securing part.

37. The method of claim 36 wherein the moving of the first and second members causes a tissue piercing element of the first member to pierce tissue, the method further comprising deploying the securing element through the tissue piercing element.

38. The method of claim 36 wherein the moving of the first and second members causes first and second tissue piercing elements of the first member to pierce tissue, the method further comprising deploying first and second elements of the securing element each through one of the first and second tissue piercing elements.

39. The method of claim 36 wherein the engaging tissue includes engaging stomach tissue beyond an esophageal junction.

40. The method of claim 36 further comprising piercing the tissue with a third member of the distal end effector prior to engaging the tissue with the first and second members.

41. The method of claim 36 wherein the moving of the distal end effector relative to the elongated member includes moving the distal end effector in the second plane generally perpendicular to the first plane.

* * * * *

UNITED STATES PATENT AND TRADEMARK OFFICE
CERTIFICATE OF CORRECTION

PATENT NO.    : 6,494,888 B1
DATED         : December 17, 2002
INVENTOR(S)   : Michael D. Laufer, Jeffrey C. Cerier and Amos G. Cruz It is certified that error appears in the above-identified patent and that said Letters Patent is hereby corrected as shown below:

<u>Title page,</u>
Item [56], U.S. PATENT DOCUMENTS, please change "6,325,503 B1" to -- 6,352,503 --.
OTHER PUBLICATIONS, "Hill, LD et al." reference please insert -- in -- before "vivo"
Replace "kadikramanathan" with -- kadirkamanathan --
"Janssen, et al.," reference, replace "trees" with -- teres --
Item [57], ABSTRACT, after "the" remove ":"

<u>Column 2,</u>
Lines 59-60, replace "gastroesoplageal" with -- gastroesophageal --

<u>Column 3,</u>
Line 32, remove "," after "access"

<u>Column 5,</u>
Line 20, remove "," after "overtube"

<u>Column 6,</u>
Line 2, replace "bars" with -- t-bars --

UNITED STATES PATENT AND TRADEMARK OFFICE
CERTIFICATE OF CORRECTION

PATENT NO. : 6,494,888 B1
DATED : December 17, 2002
INVENTOR(S) : Michael D. Laufer, Jeffrey C. Cerier and Amos G. Cruz It is certified that error appears in the above-identified patent and that said Letters Patent is hereby corrected as shown below:

Column 10,
Line 56, replace "fist" with -- first --

Signed and Sealed this

Twenty-ninth Day of July, 2003

JAMES E. ROGAN
*Director of the United States Patent and Trademark Office*